United States Patent [19]

Lee

[11] Patent Number: 4,513,754

[45] Date of Patent: Apr. 30, 1985

[54] BIOPSY AND ASPIRATION UNIT WITH A REPLACEABLE CANNULA

[75] Inventor: Peter F. Lee, Edina, Minn.

[73] Assignee: Southland Instruments, Inc., Edina, Minn.

[21] Appl. No.: 622,100

[22] Filed: Jun. 19, 1984

Related U.S. Application Data

[63] Continuation of Ser. No. 306,305, Sep. 28, 1981, abandoned, and a continuation-in-part of Ser. No. 88,818, Oct. 26, 1979, Pat. No. 4,314,565, which is a continuation-in-part of Ser. No. 883,263, Mar. 3, 1978, abandoned, which is a continuation-in-part of Ser. No. 706,130, Jul. 16, 1976, abandoned.

[51] Int. Cl.³ .............................................. A61B 10/00
[52] U.S. Cl. ................................... 128/753; 128/754; 604/240
[58] Field of Search .............. 128/753, 754, 752, 751, 128/310; 604/264, 272, 283, 240, 241, 243; 279/20, 42, 40, 48, 123, 1 J, 1 ME; 433/147

[56] References Cited

U.S. PATENT DOCUMENTS

| | | | |
|---|---|---|---|
| 449,246 | 3/1891 | Graham | 279/42 |
| 1,045,886 | 12/1912 | Reay | 279/42 |
| 1,585,934 | 5/1926 | Muir . | |
| 2,198,319 | 4/1940 | Silverman . | |
| 2,219,605 | 10/1940 | Turkel | 128/753 |
| 2,426,535 | 8/1947 | Turkel . | |
| 2,496,111 | 1/1950 | Turkel . | |
| 2,516,492 | 7/1950 | Turkel . | |
| 3,186,408 | 6/1965 | Jacob . | |
| 3,477,423 | 11/1969 | Griffith . | |
| 3,598,108 | 8/1971 | Jamshidi et al. . | |
| 3,628,524 | 12/1971 | Jamshidi . | |
| 3,630,192 | 12/1971 | Jamshidi . | |
| 3,850,158 | 11/1974 | Elias et al. . | |
| 3,893,445 | 7/1975 | Hofsess . | |
| 4,010,737 | 3/1977 | Vilaghy et al. . | |
| 4,099,518 | 7/1978 | Baylis et al. . | |
| 4,142,517 | 3/1979 | Stavropoulos et al. . | |
| 4,177,797 | 12/1979 | Baylis et al. . | |
| 4,256,119 | 3/1981 | Gauthier . | |
| 4,258,722 | 3/1981 | Sessions et al. . | |
| 4,262,676 | 4/1981 | Jamshidi | 128/754 X |
| 4,266,555 | 5/1981 | Jamshidi . | |

FOREIGN PATENT DOCUMENTS

| | | | |
|---|---|---|---|
| 244467 | 1/1948 | Switzerland | 604/166 |
| 379267 | 4/1973 | U.S.S.R. . | |

Primary Examiner—Michael H. Thaler
Attorney, Agent, or Firm—Merchant, Gould, Smith, Edell, Welter & Schmidt

[57] ABSTRACT

A bone marrow biopsy and aspiration needle unit is disclosed. The unit includes a holding device, with a longitudinal bore therethrough, comprising a collect chuck and handle grips, a replaceable cannula to be interlockably mounted in the holding device, with the cannula's lumen in alignment with the longitudinal bore, and an elongated stylet releaseably mounted in the aligned bores. When the needle unit is also to be used for aspiration, a second cannula of a diameter less than the first cannula is inserted through the aligned bores in the holding device and the first cannula.

2 Claims, 15 Drawing Figures

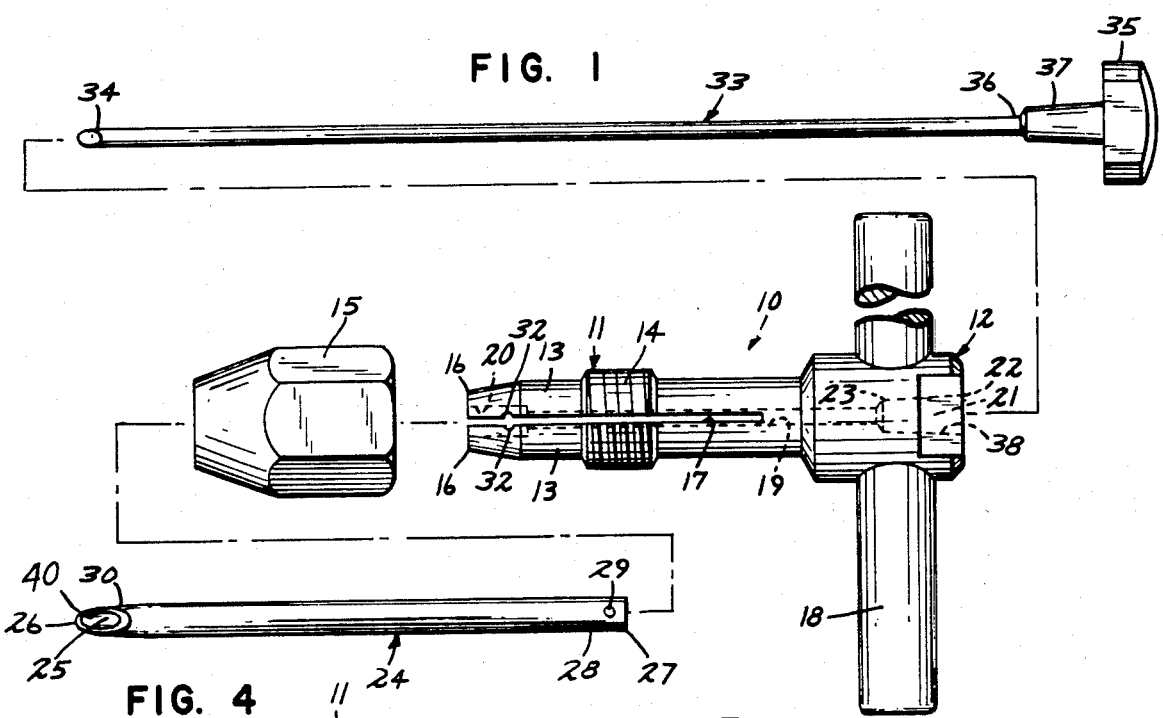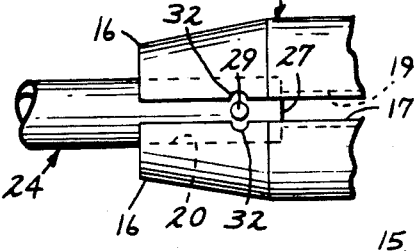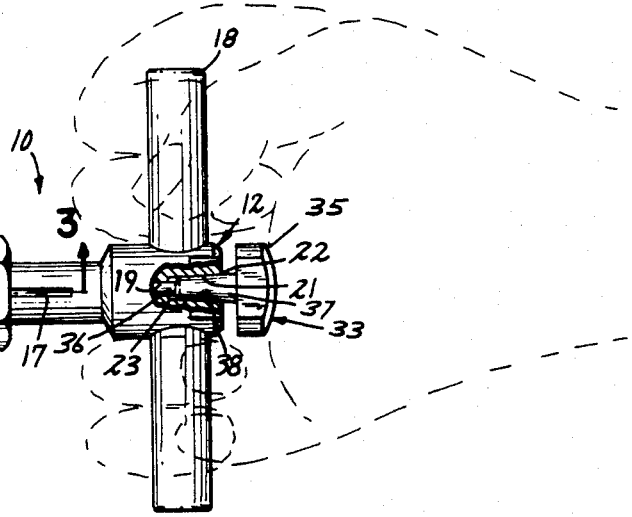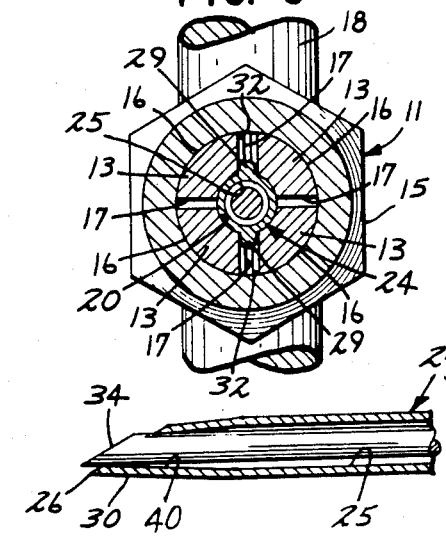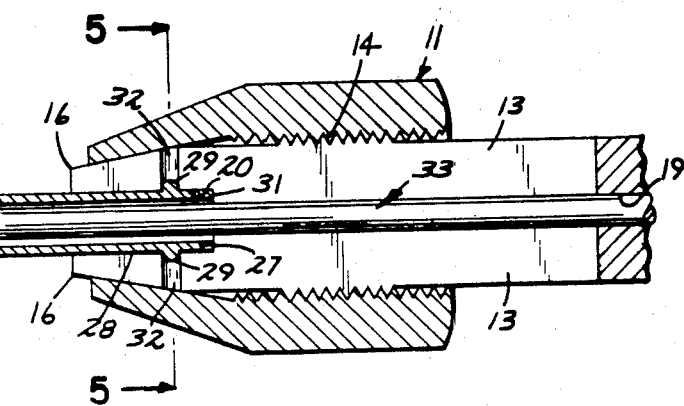

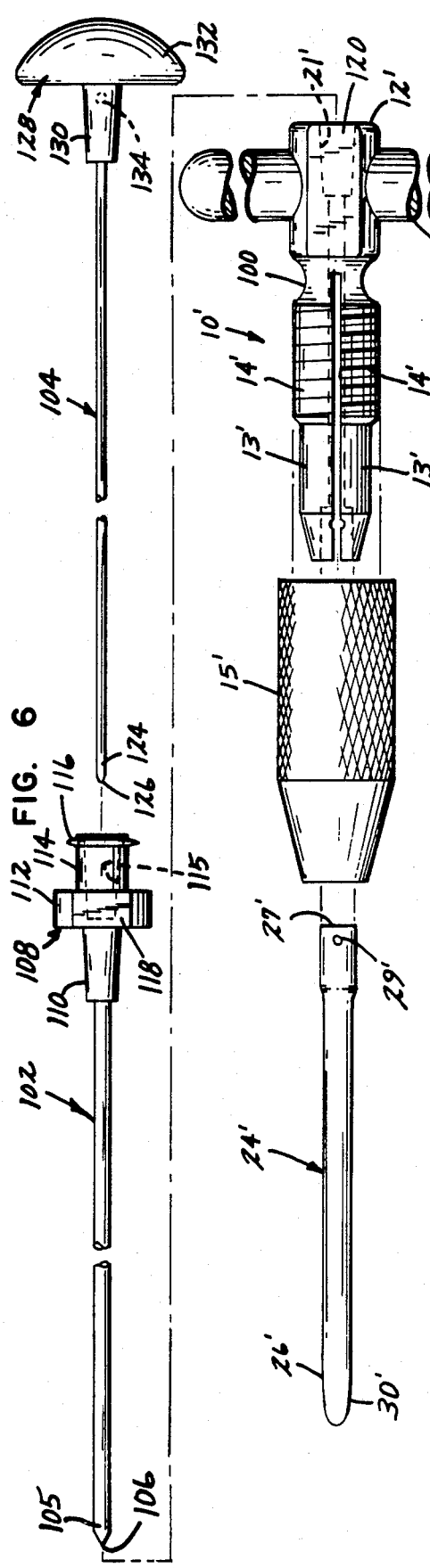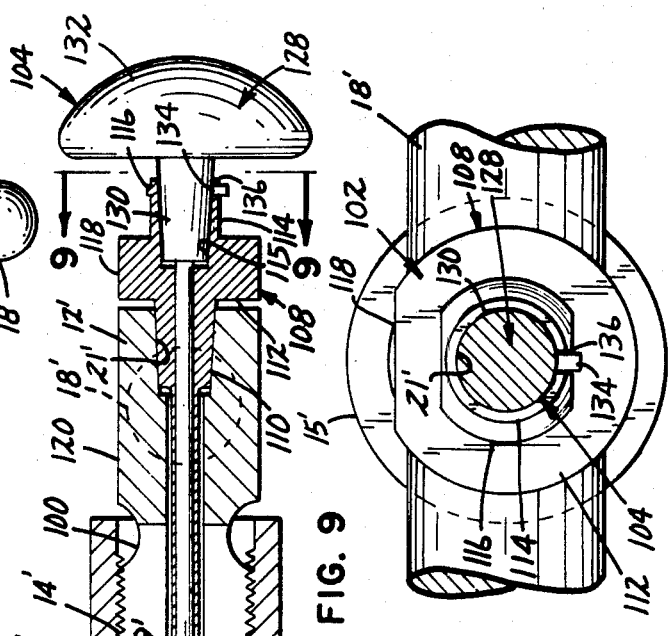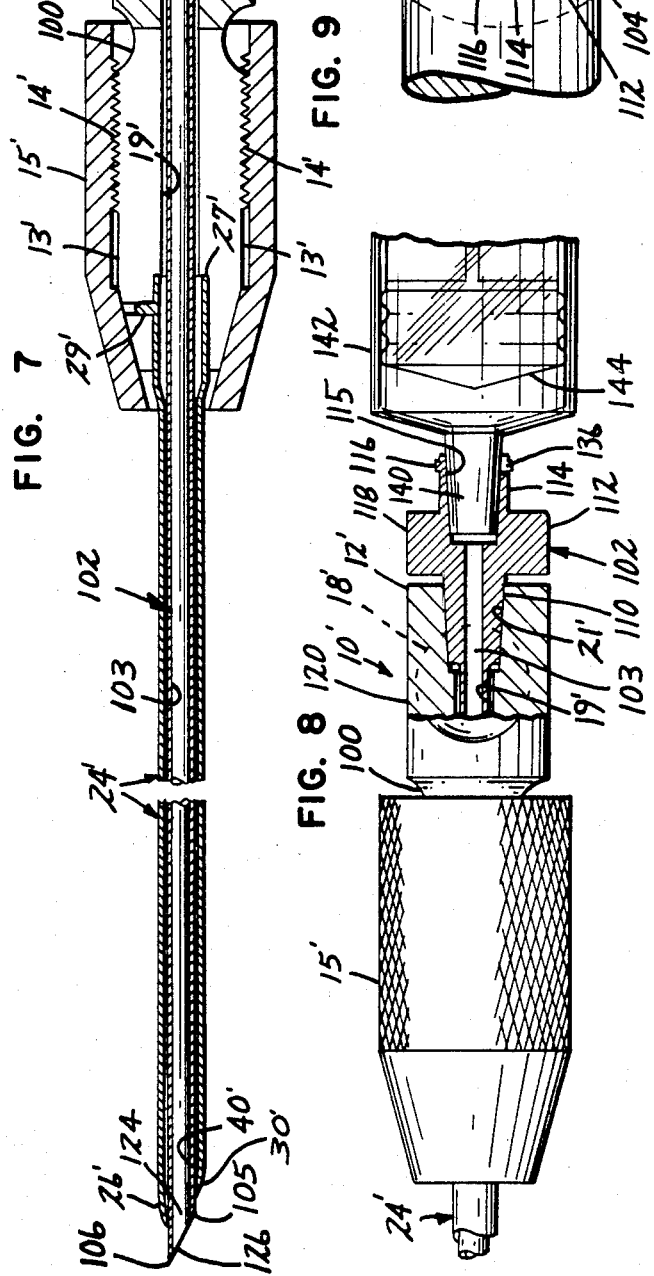

BIOPSY AND ASPIRATION UNIT WITH A REPLACEABLE CANNULA

CROSS-REFERENCE TO PRIOR APPLICATIONS

This is a continuation of application Ser. No. 306,305, filed Sept. 28, 1981, abandoned, and a continuation-in-part of application Ser. No. 88,818, filed Oct. 26, 1979, now U.S. Pat. No. 4,314,565 which is a continuation-in-part of application Ser. No. 883,263, filed Mar. 3, 1978, now abandoned, which is a continuation-in-part of Ser. No. 706,130, filed July 16, 1976, abandoned.

TECHNICAL FIELD

This invention relates to the field of surgical tools and instruments. More particularly, it relates to the field of devices used to collect bone marrow tissue and fluid specimens for biopsy purposes and the cannulas used in devices of this type.

BACKGROUND OF THE INVENTION

The advantages of examination of a bone marrow specimen undiluted with blood are well-known. Such an examination is essential for the evaluation of many hematologic disorders. A variety of devices have been used for collecting bone marrow specimens. Early bone marrow biopsies were taken from the sternum in operating-room procedures with scoop-like devices. Nonincisional methods utilizing the posterior iliac crest have proven less costly and less dangerous to the patient, and therefore more satisfactory. Such methods involve the introduction of a needle-like collecting device through the skin tissue, and the penetration of the bone cortex with the collecting device to take a small specimen of bone marrow tissue. Because of the pressure needed to bore through the cortex of the bone, and the subsequent cutting through of the trabeculae of the bone marrow, the cutting/collecting needles of prior devices have included integral finger grips of sturdy construction, such as those disclosed in Jamshidi, U.S. Pat. No. 3,628,524. The presence of such sturdy integral grips on the prior art collecting devices has made such devices expensive to use and maintain: the relatively high initial cost of the devices precludes one-time use, and multiple-time use requires resterilization of the device prior to each use and resharpening of the cutting edges. Needle lumens are difficult to clean. Tissue or proteinaceous matter left in the lumen can result in pyrogens that are unaffected by heat sterilization. Resharpening requires time and special skills. Thus, the amount of handling required by the prior art devices leads to high costs and increased chance for human error.

It is often desirable to aspirate fluids from bone tissue in addition to taking bone marrow tissue itself. Numerous devices have been available to aspirate fluids from bone tissue. Such prior art aspiration devices, however, have either been separate from the prior art devices used to take bone marrow tissue samples, or have used a bone marrow biopsy unit for aspiration. However, a bone marrow biopsy unit generally does not have the optimum diameter for aspirating fluids.

SUMMARY OF THE INVENTION

This invention provides a biopsy device that will allow for the interchange of various lengths and gauges of presterilized, pyrogen-free, single-use needles capable of obtaining and retrieving a superior histologic, undistorted bone marrow specimen at an economical cost and with minimum patient discomfort. This is accomplished in the present invention by utilizing a permanent needle-holding means and a replaceable cutting-/collecting needle, or cannula, in conjunction with a stylet. The cannula is a hollow needle with an inner and outer taper at its distal end. The holding means incorporates a collet chuck and handle grips. The holding means has a bore along its longitudinal axis to accommodate the stylet. Since, in use, strong compression, tension, and twisting forces are applied along and around the longitudinal axis of the unit, the cannula must be securely mounted in the holding means to prevent any slippage or dislodging of the cannula during its insertion and removal. This secure mounting is achieved by counterboring the jaw portion of the collet chuck to accommodate a replaceable cannula, which is of a generally larger diameter than the longitudinal bore in the holding means. The interface of the jaw counterbore with the longitudinal bore defines an annular end wall, against which the proximal end of the cannula abuts when mounted, thus preventing the cannula from slipping further into the holding means while being inserted through the bore cortex. One embodiment of the jaw counterbore is the provision of at least one recessed portion, which coincides with at least one raised portion on the external proximal end surface portion of the cannula, so that when the proximal end of the cannula is placed in the jaw counterbore and the jaws are tightened around the cannula by tightening the collar nut of the collet chuck, the raised portion of the cannula interlocks with the recessed portion of the jaw counterbore. This interlock prevents movement of the cannula around the longitudinal axis of the unit when a twisting force is applied thereto, and it also prevents the cannula from slipping out of the holding means when a pulling force is exerted on the holding means to remove the cannula from the bone cavity.

In the present invention, another embodiment of the interlock means for securely mounting the cannula in the holding means is the design and construction of the proximal end portion of the cannula as an elliptical portion extending from the remaining greater length of the cannula which has a circular cross-section. The outer surface of the proximal end portion is left unobstructed, without any raised portions. When the elliptical proximal end portion is placed into the jaw counterbore and the jaws tightened around the cannula by tightening the collar nut of the collet chuck, the elliptical proximal end portion of the cannula is interlocked between the jaws. This interlock prevents movement of the cannula around the longitudinal axis of the unit when a twisting force is applied. The cannula is also prevented from ever being dislodged when the pulling forces are exerted on the holding means during the use of the assembled needle unit as the elliptical portion cannot pass through the circular bore of the collar nut. The single piece construction of the cannula ensures a secure and reliable holding of the proximal end portion within the holding means. Thus, the structural advantages of a one-piece cannula as well as the advantages of an inexpensive, replaceable cannula are achieved in the present invention.

The invention is also an improvement directed to a needle unit capable of both retrieving a bone marrow specimen and aspirating fluids. In order to accomplish this dual function, the needle unit includes a second cannula which has an outer diameter less than the inner diameter of the cannula and the bore through the holding means. In this manner, the second cannula is inserted through the top of the holding means and passes through the longitudinal bore therein and through the hollow interior of the first cannula. The second cannula has a hollow interior extending throughout its entire length of an inner diameter appropriate for aspirating fluids. The outer end of the second cannula friction fits within a counterbore in the top of the holding means. A second stylet is inserted through the hollow interior of the second cannula during the insertion of the needle unit into a bone. In order to aspirate a fluid sample, the stylet is removed and an empty syringe is friction fit into the top of the second cannula. By withdrawing the plunger of the syringe, a fluid sample is aspirated. After the aspiration procedure has been accomplished, the second cannula can be removed and the first stylet replaced therefor. The needle unit can thereafter be moved further into the bone and the first stylet removed at the appropriate point to collect a bone marrow tissue specimen.

BRIEF DESCRIPTION OF THE DRAWINGS

FIG. 1 is an exploded elevation of the biopsy needle unit;

FIG. 2 is a view in elevation of the assembled biopsy needle unit;

FIG. 3 is a sectional view of a portion of the biopsy needle unit as seen from the line 3—3 of FIG. 2;

FIG. 4 is a fragmentary plane view of a portion of FIG. 2 with parts removed therefrom;

FIG. 5 is a sectional view as seen from the line 5—5 of FIG. 3;

FIG. 6 is an exploded elevation of the needle unit for use in aspirating fluids;

FIG. 7 is a longitudinal sectional view, partially broken away, of the assembled needle unit for aspirating fluids;

FIG. 8 is a partial view in elevation, partially broken away, illustrating a syringe inserted into the second cannula;

FIG. 9 is a view taken generally along line 9—9 of FIG. 7;

DESCRIPTION OF THE PREFERRED EMBODIMENT

Figure 10:
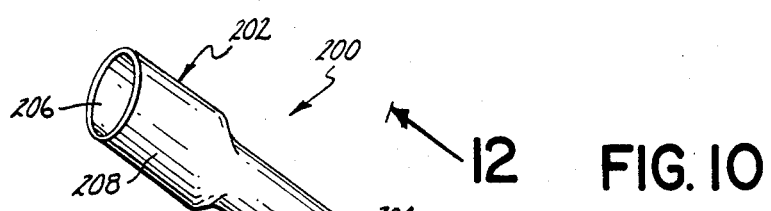
FIG. 10 is a perspective view of the replaceable cannula of the present invention.
Figure 14:
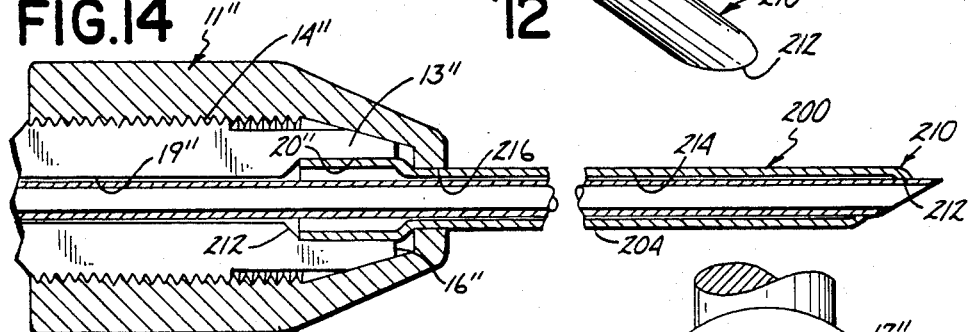
FIG. 14 is a sectional view of a portion of the assembled needle unit as seen from line 14—14 of FIG. 13.

FIG. 1 shows the elements of a bone marrow biopsy unit. Generally T-shaped holding means 10 include a collet chuck 11 and a head portion 12. Collet chuck 11 comprises a plurality of arms 13 with external threading 14 thereon to engage collar nut 15. Each arm 13 terminates in a jaw portion 16, and is separated from each other arm 13 by a compressible, generally planar space, or slot 17, running the length of each arm 13. A handle 18 extends from head portion 12 at generally right angles to the longitudinal axis of holding means 10. A longitudinal bore 19 of circular cross section runs along the longitudinal axis and through head portion 12 and collet chuck 11. A first counterbore 20 of uniform circular cross section runs along the longitudinal axis through jaw portions 16, and a second counterbore 21 runs along the longitudinal axis in head portion 12. Second counterbore 21 tapers uniformly from a first diameter 22 to a smaller, second diameter 23, which is larger than the diameter of longitudinal bore 19.

A replaceable cannula 24 has a bore, or lumen 25, an open distal end 26, which defines a cutting edge outwardly beveled and obliquely disposed to the longitudinal axis of cannula 24, an open proximal end 27, and an external proximal end surface portion 28 with raised portions. In this embodiment two hemispherical beads 29 are annularly disposed 180° apart thereon, as indicated in FIGS. 3 and 5. Cannula 24 has a generally circular cross section of uniform inside and outside diameter along the major portion of its length and internal and external distal end portions 40 and 30 uniformly tapered toward distal end 26.

First counterbore 20 is of a diameter generally equal to the outside diameter of cannula 24 at proximal end 27. Said diameter is larger than the diameter of longitudinal bore 19. An annular end wall 31 is formed at the interface of longitudinal bore 19 and first counterbore 20.

Jaw portions 16 have recesses, grooves 32 in the preferred embodiment, to interlock with beads 29 when cannula 24 is mounted in holding means 10. Grooves 32 are generally in the planes defined by slots 17 and are along an axis transverse to the longitudinal axis of the holding means 10, as depicted in FIGS. 3 and 5. Each groove 32 has a semicircular cross section of radius corresponding to the radii of beads 29.

Beads 29, grooves 32, and end wall 31 comprise a means for interlockingly mounting cannula 24 in holding means 10, which is accomplished by placing proximal end 27 in first counterbore 20, as shown in FIG. 4, and tightening collar nut 15 as shown in FIG. 3. When so mounted, lumen 25 is aligned with longitudinal bore 19.

An elongated stylet 33 has distal end 34 defining a sharpened cutting edge obliquely disposed to the longitudinal axis of stylet 33 at an angle equal to that at which distal end 26 is disposed to the longitudinal axis of cannula 24, as shown in FIG. 3. Stylet 33 has a cap portion 35 at its proximal end 36 having an elongated stem portion 37. Stem portion 37 has a tapered circular cross section corresponding to that of second counterbore 21. When stylet 33 is releasably mounted in the aligned longitudinal bore 19 of holding means 10 and lumen 25 of the mounted cannula 24, as shown in FIG. 3, stem portion 37 frictionally engages the interior surface 38 of second counterbore 21 as shown in FIG. 2, and distal end 34 extends a predetermined distance beyond distal end 26 to prevent bone matter from entering lumen 25 while the unit is boring through the bone cortex to the bone cavity. In the preferred embodiment, the predetermined distance is two millimeters.

In use, replaceable cannula 24 is interlockingly mounted in holding means 10, and stylet 33 is releasably mounted in the aligned longitudinal bore 19 and lumen 25 with stem portion 37 frictionally engaging interior surface 38 of second counterbore 21. Cannula 24, with stylet 33 in place, is then inserted through the skin tissue of a patient to the bone cortex.

Longitudinal and twisting forces are applied to holding means 10 until distal ends 26 and 34 enter the bone cavity, at which time stylet 33 is removed from aligned bore 19 and lumen 25. Cannula 24 is then forced several centimeters further into the bone cavity to collect a specimen of marrow tissue in lumen 25, after which cannula 24 is removed from the bone cavity and patient by exerting a pulling force on holding means 10. The specimen is removed from lumen 25 by first removing cannula 24 from holding means 10, and then inserting stylet 33 into lumen 25 by way of distal end 26 and gently probing the specimen to force it out of lumen 25 at proximal end 27.

Cannula 24, being a relatively inexpensive element of the unit, can be disposed of before resterilization and resharpening are required, and replaced by a new, presterilized cannula of the requisite length and gauge for use in subsequent specimen-gathering instances, thus accomplishing the objectives of the invention.

FIGS. 6–9 illustrate an embodiment which can be used to aspirate fluid from bone tissue, in addition to extracting bone marrow tissue. Portions of the needle unit illustrated in the FIGS. 6–9 which are similar portions of the unit illustrated in FIGS. 1–5, will be designated by like primed numerals.

The holding means 10' and the replaceable cannula 24' are the same as the holding means 10 and the cannula 24, except in the following minor details. The taper of the distal end 26' of the cannula 24' is reduced. The open proximal end 27' is flared outwardly to a greater diameter than the remaining portion of the cannula 24'; and only a singular bead 29' is utilized. The collar nut 15' is slightly longer than the collar nut 15 and has a round knurled outer surface. The external threading 14' on the arms 13' extends over a slightly longer longitudinal length. The outer ends of the handle 18' are rounded. An annular cutout 100 is formed in the holding means 10' at a location between the threaded portion 14' of the arms 13' and the head portion 12'.

So that the needle unit can aspirate fluid in addition to extracting the bone marrow tissue, a second cannula 102 and a second stylet 104 are provided.

The second cannula has an outer diameter less than the inner diameter of the first cannula 24' and the longitudinal bore 19' of the holding means 10'. In this manner, the second cannula 102 can be received within the first cannula 24' and the holding means 10'. The second cannula 102 has a bore or lumen 103 with an inner diameter which is necessarily less than the inner diameter of the first cannula 24' and is of the proper size for the aspiration of fluids from bone tissue. The second cannula 102 has an open distal end 105 with a sharpened cutting edge 106 obliquely disposed to the longitudinal axis of the cannula 102. The second cannula 102 also has a proximal end or head portion 108. The proximal end 108 includes a tapered engagement section 110, an alignment ring 112, and a cylindrical section 114 with a coupling collar 116. The engagement section 110 has a taper which mates with the taper of the counterbore 21' so that the engagement section 110 can frictionally engage with the counterbore 21' of the holding means 10'. The alignment collar 112 has a flat 118 and the head portion 12' has a flat 120. By aligning the flat 118 with the flat 120, the angle at which the cutting edge 106 is disposed can be aligned with the angle at which the proximal end 26' is cut. See FIG. 8. The head portion 108 also has a counterbore 115 through it in alignment with the lumen 103. The counterbore 115 has an inner diameter which tapers radially outwardly from a small diameter, which is larger than the diameter of the lumen 103, to a larger diameter.

The stylet 104 has a distal end 124 with a sharpened cutting edge 126 obliquely disposed to the longitudinal axis of the cannula 102. The stylet 104 has a proximal end 128 with a tapered engagement or stem portion 130 and a cap portion 132. The stem portion 130 has a tapered circular cross section corresponding to that of the counterbore 115 of the proximal end 108 of the second cannula 102. A finger or pin 134 extends outwardly from the stem portion 130 and is received within a slot 136 formed through the cylindrical section 114 and the coupling collar 116. In this manner, the stylet 104 is frictionally held by the mating engagement between the outer surface of the stem portion 130 and the inner surface of the counterbore 115, and the angle at which the cutting edge 126 is set is aligned with the angle of the cutting edge 106 by inserting the finger 134 within the slot 136.

The needle unit is used in the following manner to obtain a fluid sample. The cannula 24', the cannula 102 and the stylet 104 are assembled and inserted into a bone cavity to a point where a fluid sample is to be taken. Thereafter the stylet 104 is removed and a tip 140 of a syringe 142 is inserted into the counterbore 115. A plunger 144 of the syringe 142 is pulled back within a cylinder of the syringe 142 in order to aspirate fluid. The fluid is drawn through the cannula 102 into the cylinder of the syringe 142. The syringe is thereafter removed from the second cannula 102 and the fluid in the syringe can thereafter be removed from the syringe 142 for further testing or treatment. If a bone tissue sample is also required, the cannula 24' can be further inserted into the bone tissue in the same manner as the cannula 24.

In the present invention, the replaceable cannula and its use in an assembled needle unit is illustrated in FIGS. 10 through 15. In the discussion of the invention which follows, portions of the needle unit which are the same as those in the unit illustrated in FIGS. 6–9 will be designated by like numerals. It is to be understood, however, that the replaceable cannula 200 shown in FIGS. 10–15 can be readily used in a needle unit of the type shown in FIGS. 1–5.

In the generally T-shaped holding means 10'' used with the present invention, a collet chuck 11'' and a head portion 12'' are substantially similar to those shown in FIGS. 1–9. The collet chuck 11'' comprises a plurality of arms 13'' with an external threaded portion 14'' for engaging collar nut 15''. Each arm 13'' terminates in a jaw portion 16'', and is separated from each other by a compressible generally planar space, or slot, 17'' running the length of each arm 13''. The jaw portions 16'' appear as a segmented ellipse as can be seen from FIG. 15. A handle 18'' extends from head portion 12'' at generally right angles to the longitudinal axis of holding means 10''. A longitudinal bore 19 of circular cross-section extends through head portion 12'' and into collet chuck 11'' to just past or up to a point within the collet chuck 11'' corresponding to the distal end edge of the threaded portion 14''. A counterbore 20'' of uniform elliptical cross-section extends along the longitudinal axis through jaw portions 16'' to a point near the end of the first bore 19''. The counterbore 20'' is joined with the first bore 19" by a sloping surface 212 which forms an end wall or interface between the two bores.

Figures 11, 12:
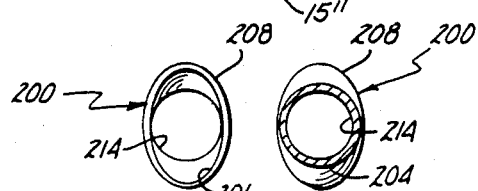
FIG. 11 is a view in elevation of the replaceable cannula shown in FIG. 10 as viewed from the open proximal end of the cannula.
FIG. 12 is a sectional view of a portion of the replaceable cannula as seen from line 12—12 of FIG. 10.
Figure 15:
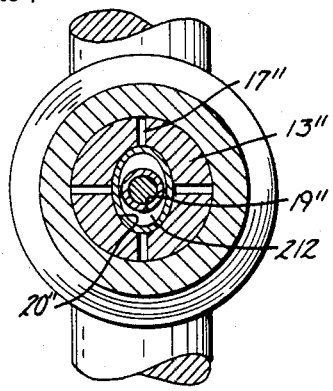
FIG. 15 is a sectional view of a portion of the assembled needle unit as seen from line 15—15 of FIG. 13.
Figure 13:
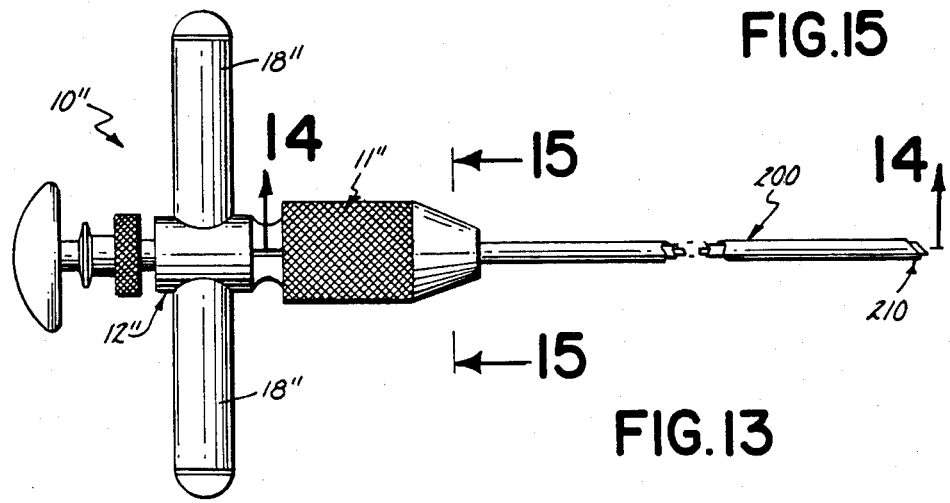
FIG. 13 is a view in elevation of the assembled needle unit capable of aspirating fluids in which the replaceable cannula of FIG. 10 is used.

The replaceable cannula 200 of the present invention is shown in prespective in FIG. 10. The replaceable cannula 200 of the present invention has a bore, or lumen, 214, a distal end porton 210, an open distal end 212 which defines a cutting edge outwardly beveled and obliquely disposed to the longitudinal axis of the cannula 200, a proximal end portion 202, an open proximal end 206, and a smooth, unobstructed external proximal end surface 208. The proximal end portion 202 is an ellipticity in contrast to the remaining elongated body portion 204 which has a generally circular cross-section along its length. The ellipticity of the proximal end portion 202 is designed and constructed as a protruding portion formed from the same piece as the remaining cannula portion 204. The proximal end portion thus has an elliptical or oval cross-section. The different cross-sections of the two portions of the cannula 200 can be more clearly understood from a study of FIGS. 11 and 12. FIG. 11 is an elevational view of the cannula 200 as viewed from the proximal end 206.

When the proximal end portion 202 of the cannula 200 is placed in the jaw counterbore 20" it is inserted a sufficient length so that the proximal end 206 abuts the end wall 212. The jaws 16" are tightened around the cannula 200 by tightening the collar nut 15" of the collet chuck 11". The interior jaw surfaces contact the proximal end portion exterior surface 208 and securely grasp the proximal end portion 202 preventing any turning or twisting movement of the cannula. See FIG. 15. Due to the elliptical configuration of the proximal end portion and the circular diameter of the bore 216 which extends through the collet chuck 11" there can be no release or dislodging of the cannula 200 from the holding means 10" as the elliptical proximal end portion cannot pass through the circular bore 216. The stainless steel construction is of sufficient strength to resist deforming from the pulling forces and this will maintain the elliptical cross-section. With the cannula end 206 abutting the end wall 212, longitudinal movement of the cannula 200 within the holding means 10" is also prevented.

The cannula 200 is formed from a single piece of stainless steel. Great strength is achieved in the cannula 200 of the present invention as a result of the one-piece construction. Despite the significant twisting and pulling forces involved in the use of the assembled needle unit, the construction of the replaceable cannula 200 has proven reliable and durable. It is virtually impossible for a human being using either the needle unit shown in FIGS. 1-5 or the needle and aspirating unit shown in FIGS. 6-9 to exert the forces which would be necessary to deform the stainless steel in order to dislodge the cannula of the present invention from the unit while inserting or withdrawing the needle unit from the patient.

Cannula 200 is a relatively inexpensive item and as such it can be used once and then disposed of before resterilization and/or resharpening are necessary. A replacement cannula 200 which is new and presterilized can then be used for subsequent specimen-gathering.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent extended by the broad general meaning of the terms in which the appended claims are expressed.

What is claimed is:

1. An improved bone marrow biopsy needle unit, comprising:

holding means including a collet chuck and a head portion aligned coaxially so that a line running along the common axis defines a longitudinal axis of said holding means, a bore of circular cross section along said longitudinal axis through said head portion and said collet chuck, and handle means extending from said head portion generally at right angles to said longitudinal axis, said collet chuck comprising a plurality of arms with external threading thereon, adjacent arms being separated by a generally longitudinally extending slot, each arm terminating in a jaw portion, and a collar nut to threadedly engage and radially compress said arms, each arm having an interior surface, said interior surfaces defining a segmented ellipse when said arms are not compressed by said collar nut;

an elongated stylet, of predetermined length and gauge of generally uniform circular cross-section mounted in said aligned bores, said stylet having a distal end, a proximal end, and a cap portion at said proximal end;

engaging means on both said stylet and said head portion cooperating to releasably engage said stylet and said holding means;

and a replaceable cannula, of predetermined length and gauge, of uniform hollow cylindrical configuration throughout the major portion of its length, having an open distal end, defining a cutting edge, an open proximal end, and an external proximal end surface portion;

said replaceable cannula being of single-piece, stainless steel construction;

said proximal end portion having a generally elliptical cross-section and formed as a continuous extension of said cannula major portion, said proximal end portion being adapted to be releasably mounted in said collet chuck with a bore thereof being coaxially aligned with said bore of said holding means, whereby said cannula is prevented from movement along or around said longitudinal axis by said proximal end portion being securely grasped by said arms of said collet chuck with said proximal end substantially abutting said collar nut and said collar nut compressing said interior surfaces of said arms of said collect chuck against said proximal end as said collar nut is threaded onto said collet chuck.

2. An improved needle unit comprising:

holding means including a collet chuck and a head portion aligned coaxially so that a line running along the common axis defines a longitudinal axis of said holding means, a bore of circular cross-section along said longitudinal axis through said head porton and said collet chuck, and handle means extending from said head portion generally at right angles to said longitudinal axis, said collet chuck comprising a plurality of arms with external threading thereon, adjacent arms being separated by a generally longitudinally extending slot, each arm terminating in a jaw portion, and a collar nut to threadedly engage and radially compress said arms, each arm having an interior surface, said interior surfaces defining a segmented ellipse when said arms are not compressed by said collar nut;

a replaceable cannula, of predetermined length and gauge, having an open distal end, an elongate body portion of generally circular cross-section, an open proximal end and a proximal end portion;

a second cannula having an outer diameter less than the inner diameter of said first cannula and the bore through said holding means, said second cannula having a distal end for insertion into said first cannula and a proximal end which extends out of said head portion when said second cannula is inserted into said first cannula and holding means in an operative position, said proximal end of said second cannula having a counterbore sized to frictionally engage a tip of a syringe; and a stylet having an outer diameter less than the inner diameter of said second cannula for insertion into said second cannula, and means for releasably holding said stylet within said second cannula;

said replaceable cannula being made of stainless steel and having a single-piece construction; and said replaceable cannula proximal end portion being formed continuous with said elongate body portion and having a generally elliptical cross-section, said replaceable cannula being adapted to be releasably mounted in said collet chuck by said collar nut compressing said interior surface of said arms of said collet chuck against said proximal end for preventing movement of said replaceable cannula along or around said longitudinal axis of said holding means when said proximal end of said replaceable cannula is mounted in said collet chuck.

* * * * *